US011648325B1

(12) United States Patent
Sheng et al.

(10) Patent No.: US 11,648,325 B1
(45) Date of Patent: May 16, 2023

(54) STERILIZATION EQUIPMENT AND STERILIZATION PROCESS

(71) Applicant: Zhejiang Bocon Intelligent Equipment Co., Ltd., Zhejiang (CN)

(72) Inventors: Qiping Sheng, Zhejiang (CN); Guiming Sun, Zhejiang (CN); Fangming Sheng, Zhejiang (CN)

(73) Assignee: ZHEJIANG BOCON INTELLIGENT EQUIPMENT CO., LTD., Zhejiang (CN)

( * ) Notice: Subject to any disclaimer, the term of this patent is extended or adjusted under 35 U.S.C. 154(b) by 0 days.

(21) Appl. No.: 17/971,805

(22) Filed: Oct. 24, 2022

(30) Foreign Application Priority Data

Aug. 17, 2022 (CN) .......................... 202210988154.0

(51) Int. Cl.
*A61L 2/20* (2006.01)
*A61L 2/06* (2006.01)
(52) U.S. Cl.
CPC .................... *A61L 2/20* (2013.01); *A61L 2/06* (2013.01); *A61L 2202/15* (2013.01); *A61L 2202/17* (2013.01)

(58) Field of Classification Search
None
See application file for complete search history.

(56) References Cited

U.S. PATENT DOCUMENTS

2020/0114030 A1\* 4/2020 Shodder .................... A61L 2/26

\* cited by examiner

*Primary Examiner* — Jelitza M Perez
(74) *Attorney, Agent, or Firm* — Cooper Legal Group, LLC

(57) ABSTRACT

The present application relates to a field of sterilization and disinfection, and in particular, relates to a sterilization equipment and a sterilization process. A sterilization equipment includes a rotatable table, a heat transmission pipe, a suction pipe, a pretreatment gas pipe and a protective gas pipe; a plurality of working station modules are provided on the rotatable table; a heating pipe is provided inside the working station module and configured for communicating with the heat transmission pipe; a material port, a suction port, a first gas inlet, a second gas inlet and a reagent port are defined in the working station module; when the rotatable table is rotated, the working station module is moved to a feeding station, a pretreatment station, a pre-sterilization station, a reagent adding station, a sterilization station, a cleaning station and a discharging station in turn.

8 Claims, 3 Drawing Sheets

STERILIZATION EQUIPMENT AND STERILIZATION PROCESS

CROSS-REFERENCE TO RELATED APPLICATION

This application claims the priority and benefit of China patent application serial no. 202210988154.0, filed on Aug. 17, 2022. The entirety of the above-mentioned patent application is hereby incorporated by reference herein and made a part of this specification.

TECHNICAL FIELD

The present application relates to a field of sterilization and disinfection, and in particular, relates to a sterilization equipment and a sterilization process.

BACKGROUND ART

A sterilization equipment is used for sterilizing the product, and there are various types of sterilization equipment. At present, conventional sterilization methods include steam sterilization, ethylene oxide gas sterilization, hydrogen peroxide plasma sterilization, gaseous formaldehyde sterilization, radiation sterilization, etc. Large-scale sterilization generally adopts steam sterilization, ethylene oxide gas sterilization and radiation sterilization.

In order to increase the output of a single sterilization, the sterilization equipment has to be designed to have a large volume. However, due to the large volume of the sterilization equipment, the product will suffer from a very slow heat and moisture penetration process in the sterilization equipment, resulting in an extremely low penetration efficiency of sterilization gas and in turn a very low sterilization efficiency. For example, ethylene oxide gas sterilization needs a cycle time of 10-14 hours.

SUMMARY

In order to improve the efficiency of large-scale sterilization, the present application provides a sterilization equipment and a sterilization process.

In a first aspect, a sterilization equipment provided in the present application adopts the following technical solution.

A sterilization equipment includes a rotatable table, a heat transmission pipe, a suction pipe, a pretreatment gas pipe and a protective gas pipe; in which a plurality of working station modules are provided on the rotatable table; a heating pipe is provided inside the working station module and configured for communicating with the heat transmission pipe; and a material port, a suction port, a first gas inlet, a second gas inlet and a reagent port are defined in the working station module; when the rotatable table is rotated, the working station module is moved to a feeding station, a pretreatment station, a pre-sterilization station, a reagent adding station, a sterilization station, a cleaning station and a discharging station in turn; at the feeding station, a material to be sterilized is introduced into the working station module through the material port; at the pretreatment station, the suction pipe communicates with an interior of the working station module through the suction port, and the pretreatment gas pipe communicates with the interior of the working station module through the first gas inlet; at the pre-sterilization station, the suction pipe communicates with the interior of the working station module through the suction port; at the reagent adding station, a sterilant is introduced into the working station module through the reagent port; the suction pipe communicates with the interior of the working station module through the suction port; and the protective gas pipe communicates with the interior of the working station module through the second gas inlet; at the sterilization station, the suction pipe communicates with the interior of the working station module through the suction port; at the cleaning station, the suction pipe communicates with the interior of the working station module through the suction port; and the protective gas pipe communicates with the interior of the working station module through the second gas inlet; and at the discharging station, the sterilized material is taken out of the material port.

In the above technical solution, the sterilization equipment is designed as a rotary structure. The working station module passes the feeding station, the pretreatment station, the pre-sterilization station, the reagent adding station, the sterilization station, the cleaning station and the discharging station successively to finish the sterilization of the material inside the working station module. A plurality of working station modules may realize a continuous flow-line sterilization, improving the sterilization efficiency. The volume of the working station module in this rotary structure may be designed to be relatively small, which not only reduces the occupied area of the whole equipment and reduces cost, but also improves penetration rate in the working station module, further improving the sterilization efficiency.

In some embodiments, the working station module is configured to be further moved to a spare station when the rotatable table is rotated; the spare station is positioned between the feeding station and the discharging station; and the material to be sterilized is introduced at the spare station or a material after sterilization is taken out of the spare station.

In the above technical solution, the area of the rotatable table may be fully utilized by arranging the spare station, improving the feeding efficiency or discharging efficiency.

In some embodiments, the heat transmission pipe includes an annular water inlet pipe and an annular water outlet pipe; one end of the heating pipe communicates with the annular water inlet pipe; and the other end of the heating pipe communicates with the annular water outlet pipe.

In the above technical solution, the whole sterilization equipment shares a heating system by arranging the annular water inlet pipe and the annular water outlet pipe. The heating system could stay in a temperature constant operation state, improving the stability of the equipment and reducing the failure rate of the equipment.

In some embodiments, the material port and the reagent port are formed on a side of the working station module away from a center of the rotatable table; and the suction port, the first gas inlet and the second gas inlet are formed on a side of the working station module facing the center of the rotatable table.

In the above technical solution, the heat transmission pipe, the suction pipe, the pretreatment gas pipe and the protective gas pipe may be arranged at the center of the rotatable table, reducing the influence of pipes on the feeding, discharging and dosing processes.

In some embodiments, at least three pretreatment stations are provided; at least three cleaning stations are provided; number of the working station modules is equal to a sum of numbers of the feeding station, the pretreatment station, the pre-sterilization station, the reagent adding station, the sterilization station, the cleaning station, the discharging station and the spare station; and the plurality of working station modules are symmetrically arranged about the center of the rotatable table.

In the above technical solution, the number of the working stations may be arranged reasonably and the take-time of the sterilization equipment at each working station may be adjusted according to the required time of each process steps.

In some embodiments, the working station module has a volume of 0.1-0.99 cubic meters.

In the related art, the volume of the ethylene oxide sterilization cabinet may be up to 150 cubic meters, and the volume of the steam sterilization cabinet may be up to 30 cubic meters. In the above technical solution, the working station module has a small volume and a high penetration rate, and the average use amount of the sterilant is low.

In some embodiments, the suction pipe, the pretreatment gas pipe and the protective gas pipe are all detachably connected to the working station module, and the heat transmission pipe is detachably connected to the heating pipe.

In the above technical solution, pipes are all detachably connected to the working station module, which facilitates the rotatable table to rotate.

In a second aspect, a sterilization process provided in the present application adopts the following technical solution.

A sterilization process adopting the above sterilization equipment includes the following steps: feeding step, in which a working station module is moved to a feeding station; a material to be sterilized is introduced into the working station module through a material port; and a heat transmission pipe is connected to a heating pipe for heating the working station module;

pretreatment step, in which the working station module is moved to a pretreatment station; the heat transmission pipe is connected to the heating pipe for heating the working station module; a suction pipe communicates with an interior of the working station module through a suction port for vacuumizing the working station module; and a pretreatment gas pipe communicates with the interior of the working station module through a first gas inlet for introducing a pretreatment gas into the working station module;

pre-sterilization step, in which the working station module is moved to a pre-sterilization station; the heat transmission pipe is connected to the heating pipe for heating the working station module; and the suction pipe communicates with the interior of the working station module through the suction port for vacuumizing the working station module;

reagent adding step, in which the working station module is moved to a reagent adding station, a sterilant is introduced into the working station module through a reagent port; the heat transmission pipe is connected to the heating pipe for heating the working station module; the suction pipe communicates with the interior of the working station module through the suction port for vacuumizing the working station module; and a protective gas pipe communicates with the interior of the working station module through the second gas inlet for introducing a protective gas into the working station module;

sterilization step, in which the working station module is moved to a sterilization station; the heat transmission pipe is connected to the heating pipe for heating the working station module; and the suction pipe communicates with the interior of the working station module through the suction port for vacuumizing the working station module;

pulse cleaning, in which the working station module is moved to a cleaning station; the heat transmission pipe is connected to the heating pipe for heating the working station module; the suction pipe communicates with the interior of the working station module through the suction port for vacuumizing the working station module; and the protective gas pipe communicates with the interior of the working station module through the second gas inlet for introducing a protective gas into the working station module; and discharging step, in which the working station module is moved to a discharging station; and a material after sterilization is taken out of the material port.

In conclusion, the present application has at least one of the following beneficial technical effects:

1. the sterilization equipment is designed as a rotary structure, realizing a continuous flow-line sterilization and improving the sterilization efficiency;
2. the volume of the working station module in this rotary structure may be designed to be small, which not only reduces the occupied area of the whole equipment and reduces cost, but also improves the penetration rate in the working station module; and
3. the heating system can be shared in the rotary sterilization equipment, so that the heating system is able to stay in a constant temperature operation state, improving the stability of the equipment and reducing the failure rate of the equipment.

DETAILED DESCRIPTION

The present application is further described in detail below in combination with FIGS. 1-3.

An embodiment in the present application discloses a sterilization equipment.

Figure 1:
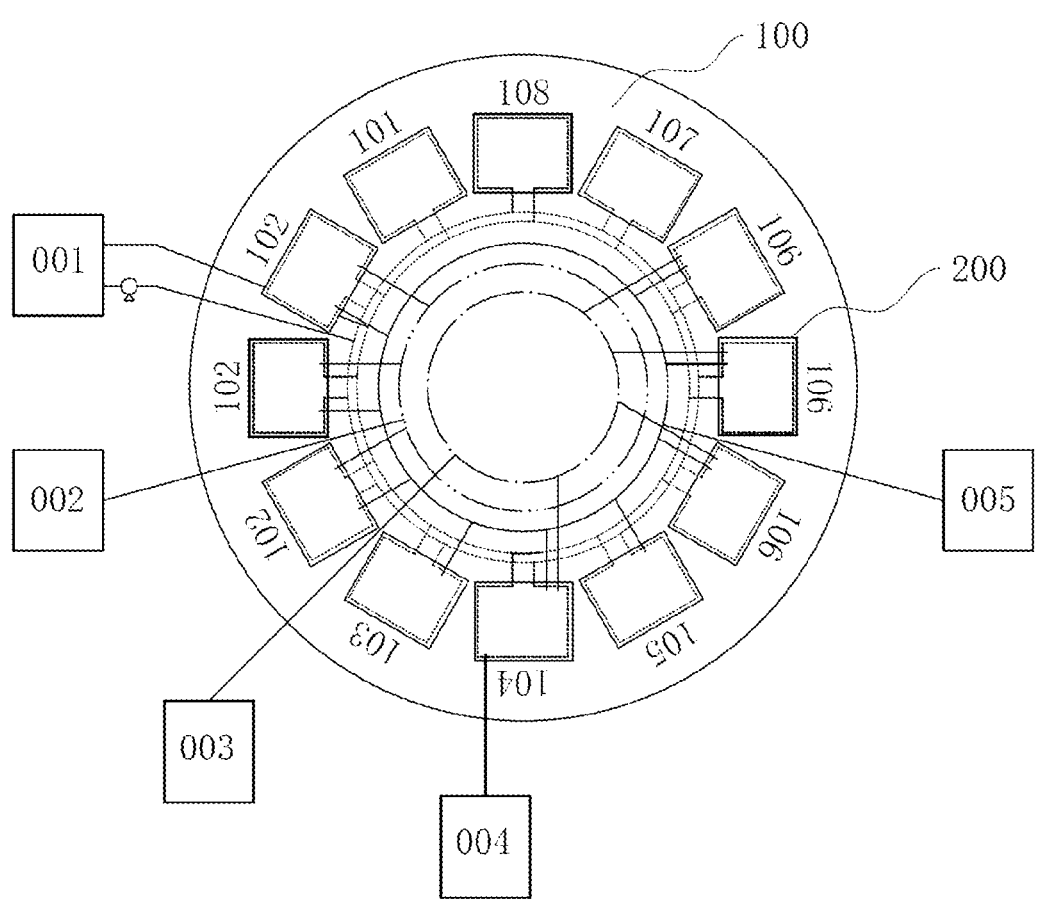
FIG. 1 illustrates a schematic diagram of the overall structure of a sterilization equipment.

Referring to FIG. 1, a sterilization equipment includes a rotatable table 100. The rotatable table 100 is horizontally arranged, and it may be rotated around a central axis thereof. In this embodiment, one feeding station 101, three pretreatment station 102, one pre-sterilization stations 103, one reagent adding station 104, one sterilization station 105, three cleaning stations 106, one discharging station 107 and one spare station 108 are successively arranged along the anti-clockwise direction of the rotatable table 100. A plurality of working station modules 200 are provided on the rotatable table 100. The number of the working station modules 200 is equal to the sum of the numbers of the feeding station 101, the pretreatment station 102, the pre-sterilization station 103, the reagent adding station 104, the sterilization station 105, the cleaning station 106, the discharging station 107 and the spare station 108. In this embodiment, there are twelve working station modules 200, and the working station modules 200 are symmetrically arranged about the center of the rotatable table 100. The spare station 108 may be used as a feeding station 101 or a discharging station 107.

Figure 2:
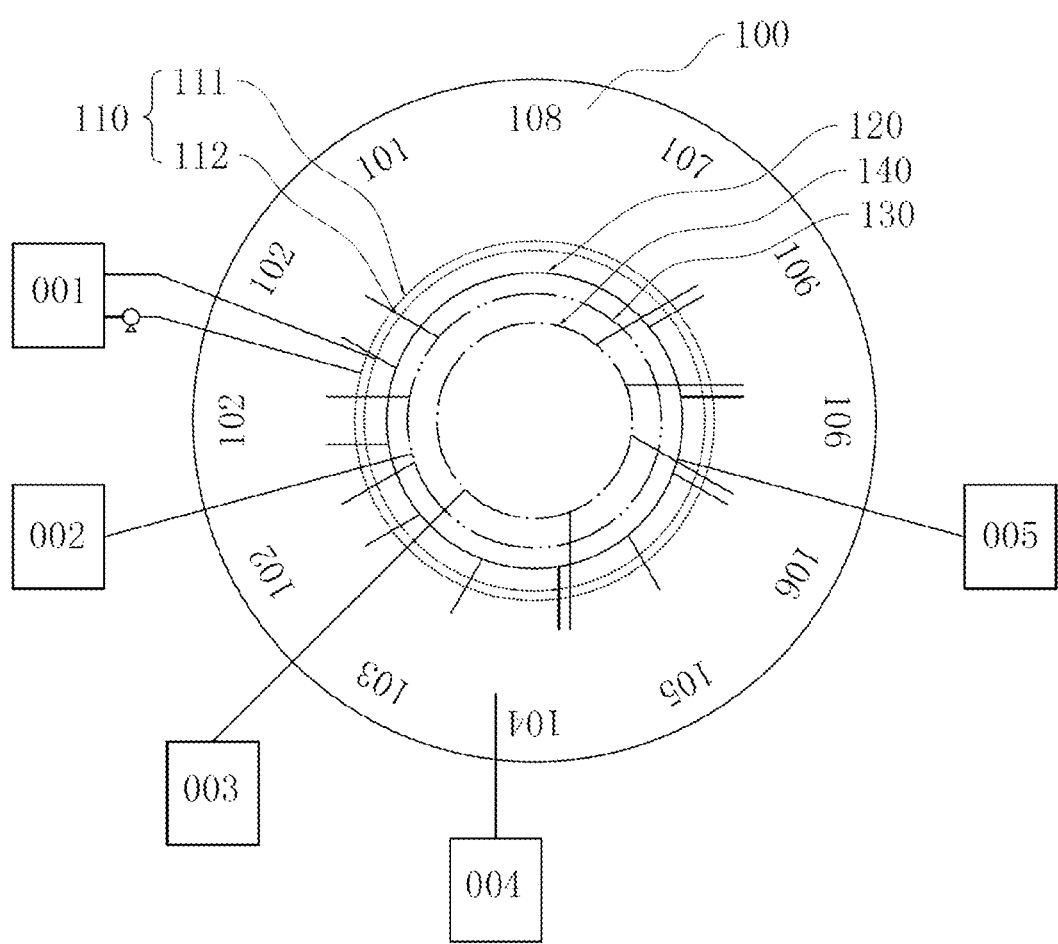
FIG. 2 illustrates a pipe layout diagram of a sterilization equipment.

Referring to FIG. 1 and FIG. 2, a sterilization equipment further includes a heat transmission pipe 110 (marked with a dashed line in the figures), a suction pipe 120 (marked with a solid line in the figures), a pretreatment gas pipe 130 (marked with a double dot dash line in the figures), a protective gas pipe 140 (marked with a dot dash line in the figures), a hot water tank 001, a pretreatment gas source 002, a protective gas source 003, a sterilization medicament source 004 and a vacuum pump 005.

Figure 3:
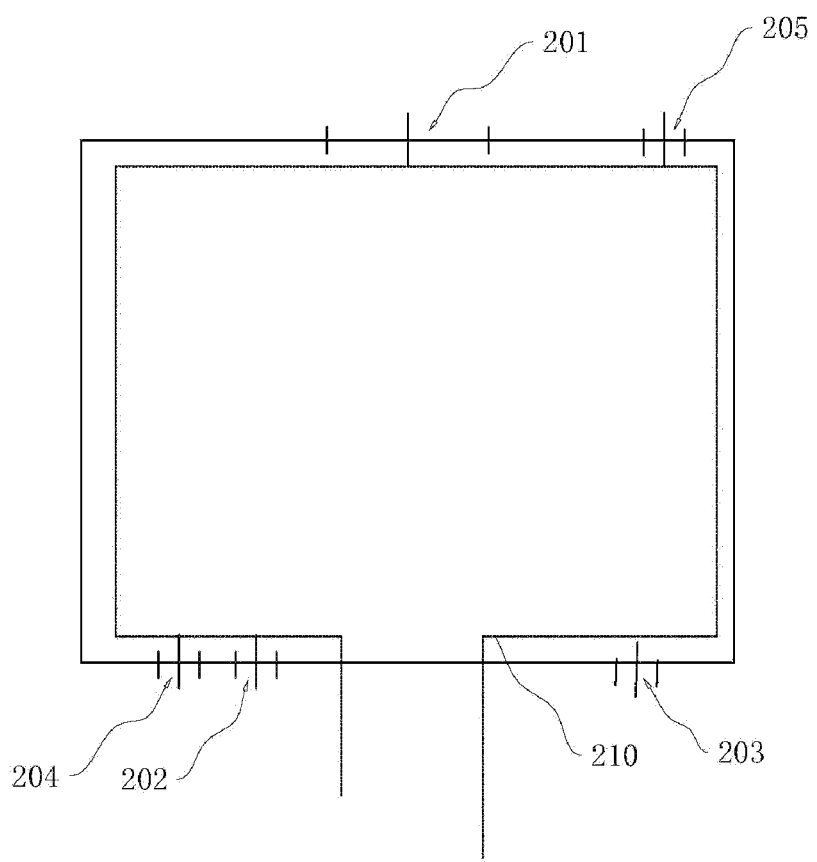
FIG. 3 illustrates a structural schematic diagram of a working station module in a sterilization equipment.

Referring to FIG. 2 and FIG. 3, a heating pipe 210 is provided inside the working station module 200. The heat transmission pipe 110 includes an annular water inlet pipe 111 and an annular water outlet pipe 112, in which the annular water inlet pipe 111 and the annular water outlet pipe 112 are coaxial with the rotatable table 100. One end of the heating pipe 210 communicates with the annular water inlet pipe 111, and the other end of the heating pipe 210 communicates with the annular water outlet pipe 112. The heat transmission pipe 110 is connected to the hot water tank 001 for heating the working station module 200. The heat transmission pipe 110 is detachably connected to the heating pipe 210.

The hot water in the hot water tank 001 is pumped to the annular water inlet pipe 111 by a water pump, and further pumped to the working station module 200 for heating the working station module 200. The cooled water after the heat transmission may flow back to the hot water tank 001 through the annular water outlet pipe 112 for being reheated.

Referring to FIG. 1 and FIG. 2, the pretreatment gas pipe 130 is configured to be annular-shaped, and be coaxial with the rotatable table 100. The pretreatment gas pipe 130 communicates with the pretreatment gas source 002. The protective gas pipe 140 is configured to be annular-shaped, and be coaxial with the rotatable table 100. The protective gas pipe 140 communicates with the protective gas source 003. The suction pipe 120 is configured to be annular-shaped, and be coaxial with the rotatable table 100. The suction pipe 120 communicates with the vacuum pump 005. The suction pipe 120, the pretreatment gas pipe 130 and the protective gas pipe 140 are all detachably connected to the working station module 200.

Referring to FIG. 1 and FIG. 3, the working station module 200 has a volume of 0.1-0.99 cubic meters. In this embodiment, the working station module 200 has a volume of 0.5 cubic meters. A material port 201, a suction port 202, a first gas inlet 203, a second gas inlet 204 and a reagent port 205 are defined in the working station module 200. The material port 201 and the reagent port 205 are formed on a side of the working station module 200 facing away from a center of the rotatable table 100; and the suction port 202, the first gas inlet 203 and the second gas inlet 204 are formed on a side of the working station module 200 facing the center of the rotatable table 100.

The material to be sterilized could be introduced in the working station module 200 through the material port 201. The material after sterilization could be taken out of the material port 201. The working station module 200 may be communicated with the suction pipe 120 through the suction port 202. The working station module 200 may be communicated with the pretreatment gas pipe 130 through the first gas inlet 203. The working station module 200 may be communicated with the protective gas pipe 140 through the second gas inlet 204. The sterilant in the sterilization medicament source 004 is able to be introduced into the working station module 200 through the reagent port 205 to sterilize the material. Generally, the material port 201, the suction port 202, the first gas inlet 203, the second gas inlet 204 and the reagent port 205 are all in a closed state. When being required to be connected to the corresponding pipe, the corresponding port is opened.

The following sterilization process is adopted to sterilize the material.

Feeding step: any one of the empty working station modules 200 is moved to the feeding station 101. The material to be sterilized is introduced into the working station module 200 through the material port 201. The heat transmission pipe 110 is connected to the heating pipe 210 for heating the material to be sterilized up to 35-75° C.

Pretreatment step: the rotatable table 100 is rotated and the working station module 200 is moved to the first pretreatment station 102. The heat transmission pipe 110 is connected to the heating pipe 210 for continuously heating the material to be sterilized. The suction pipe 120 communicates with the interior of the working station module 200 through the suction port 202. The vacuum pump 005 is started for vacuumizing the working station module 200. The pretreatment gas pipe 130 communicates with the interior of the working station module 200 through the first gas inlet 203 and the pretreatment gas is introduced into the working station module 200. In this embodiment, the pretreatment gas adopts carbon dioxide or nitrogen with a humidity between 30% RH and 90% RH. The pressure inside the working station module 200 is between −50 kPa and +200 kPa after the gas introduction.

The rotatable table 100 is rotated, the working station module 200 is moved to the other two pretreatment station 102 and the above pretreatment operation is repeated.

Pre-sterilization step: the rotatable table 100 is rotated and the working station module 200 is moved to the pre-sterilization station 103. The heat transmission pipe 110 is connected to the heating pipe 210 for continuously heating the material to be sterilized. The suction pipe 120 communicates with the interior of the working station module 200 through the suction port 202. The vacuum pump 005 is started for vacuumizing the working station module 200.

Reagent adding step: the rotatable table 100 is rotated and the working station module 200 is moved to the reagent adding station 104. The sterilization medicament source 004 communicates with the working station module 200 through the reagent port 205, and the sterilant is introduced. The heat transmission pipe 110 is connected to the heating pipe 210 for continuously heating the material to be sterilized. The suction pipe 120 communicates with the interior of the working station module 200 through the suction port 202. The vacuum pump 005 is started for vacuumizing the working station module 200. The protective gas pipe 140 communicates with the interior of the working station module 200 through the second gas inlet 204. The protective gas is introduced into the working station module 200. In this embodiment, the protective gas adopts carbon dioxide or nitrogen.

Sterilization step: the rotatable table 100 is rotated and the working station module 200 is moved to the sterilization station 105. The heat transmission pipe 110 is connected to the heating pipe 210 for continuously heating the material to be sterilized. The suction pipe 120 communicates with the interior of the working station module 200 through the suction port 202. The vacuum pump 005 is started for vacuumizing the working station module 200.

Pulse cleaning: the rotatable table 100 is rotated and the working station module 200 is moved to the first cleaning station. The heat transmission pipe 110 is connected to the heating pipe 210 for continuously heating the material to be sterilized. The suction pipe 120 communicates with the interior of the working station module 200 through the suction port 202. The vacuum pump 005 is started for vacuumizing the working station module 200. The protective gas pipe 140 communicates with the interior of the working station module 200 through the second gas inlet 204. The protective gas is introduced into the working station module 200.

The rotatable table 100 is rotated, the working station module 200 is moved to the other two cleaning station 106 and the above pulse cleaning operation is repeated.

Discharging step: the rotatable table 100 is rotated and the working station module 200 is moved to the discharging station 107. The material after sterilization is taken out of the material port 201.

The sterilization equipment in the present application has the following advantages.

The operation mode is designed to be a rotatory sterilization structure, realizing the continuous flow-line sterilization. The sterilization equipment of the present application has high sterilization capacity, small occupied area, and low cost.

The working station module 200 has a small volume, so that the penetration rate is high, and the average use amount of the sterilant is small. In addition, a part of the sterilant that needs to be discarded may be used for pre-sterilizing the product, effectively improving the using rate of the sterilant, reducing the injection amount of the sterilant in the next station, so as to save the sterilant, and reduce the pollution of the sterilant to the environment.

The rotatory sterilization equipment shares the heating system, the vacuum system, the protective gas system. These common systems may all stay in a constant pressure, constant temperature or constant humidity state, improving the stability of the equipment and reducing the failure rate of the equipment.

The pretreatment gas source used in the sterilization process may be compounded outside the cabinet. The compounded gas source may be introduced into the cabinet quickly when required, effectively shortening the operation time of the whole sterilization process and improving the operation efficiency.

The sterilant in the sterilization process may be formulated outside the cabinet and be directly introduced into the cabinet quickly, which improves the efficiency and effectively controls the concentration of the sterilant.

The above are the preferred embodiments of the present application, which are not intended to limit the protection scope of the present application. Therefore, all equivalent changes made according to the structure, shape and principle of the present application should fall within the protection scope of the present application.

What is claimed is:

1. A sterilization equipment comprising a rotatable table, a heat transmission pipe, a suction pipe, a pretreatment gas pipe and a protective gas pipe; wherein
   a plurality of working station modules are provided on the rotatable table; a heating pipe is provided inside each of the working station modules and configured for communicating with the heat transmission pipe; and a material port, a suction port, a first gas inlet, a second gas inlet and a reagent port are defined in each of the working station modules;
   when the rotatable table is rotated, each of the working station modules is moved to a feeding station, a pretreatment station, a pre-sterilization station, a reagent adding station, a sterilization station, a cleaning station and a discharging station in turn;
   at the feeding station, a material to be sterilized is introduced into each of the working station modules through the material port;
   at the pretreatment station, the suction pipe communicates with an interior of each of the working station modules through the suction port, and the pretreatment gas pipe communicates with the interior of each of the working station modules through the first gas inlet;
   at the pre-sterilization station, the suction pipe communicates with the interior of each of the working station modules through the suction port;
   at the reagent adding station, a sterilant is introduced into each of the working station modules through the reagent port, the suction pipe communicates with the interior of each of the working station modules through the suction port, and the protective gas pipe communicates with each of the interior of the working station modules through the second gas inlet;
   at the sterilization station, the suction pipe communicates with the interior of each of the working station modules through the suction port;
   at the cleaning station, the suction pipe communicates with the interior of each of the working station modules through the suction port, and the protective gas pipe communicates with the interior of each of the working station modules through the second gas inlet; and
   at the discharging station, the material after sterilization is taken out of the material port.

2. The sterilization equipment according to claim 1, wherein each of the working station modules is configured to be further moved to a spare station when the rotatable table is rotated; the spare station is positioned between the feeding station and the discharging station; and a second material to be sterilized is introduced at the spare station or a second material after sterilization is taken out of the spare station.

3. The sterilization equipment according to claim 1, wherein the heat transmission pipe comprises an annular water inlet pipe and an annular water outlet pipe; one end of the heating pipe communicates with the annular water inlet pipe; and a second end of the heating pipe communicates with the annular water outlet pipe.

4. The sterilization equipment according to claim 1, wherein the material port and the reagent port are formed on a side of each of the working station modules facing away from a center of the rotatable table; and the suction port, the first gas inlet and the second gas inlet are formed on a side of each of the working station modules facing the center of the rotatable table.

5. The sterilization equipment according to claim 2, wherein at least three of the pretreatment stations are provided; at least three of the cleaning stations are provided; a number of the plurality of working station modules is equal to a sum of the numbers of the feeding stations, the pretreatment stations, the pre-sterilization stations, the reagent adding stations, the sterilization stations, the cleaning stations, the discharging stations and the spare stations; and the plurality of working station modules are symmetrically arranged about a center of the rotatable table.

6. The sterilization equipment according to claim 1, wherein each of the working station modules has a volume of 0.1-0.99 cubic meters.

7. The sterilization equipment according to claim 1, wherein the suction pipe, the pretreatment gas pipe and the protective gas pipe are all detachably connected to each of the working station modules, and the heat transmission pipe is detachably connected to the heating pipe.

8. A sterilization process comprising the following steps:
   performing a feeding step, wherein a working station module is moved to a feeding station; a material to be sterilized is introduced into the working station module through a material port; and a heat transmission pipe is connected to a heating pipe for heating the working station module;

performing a pretreatment step, wherein the working station module is moved to a pretreatment station; the heat transmission pipe is connected to the heating pipe for heating the working station module; a suction pipe communicates with an interior of the working station module through a suction port for vacuumizing the working station module; and a pretreatment gas pipe communicates with the interior of the working station module through a first gas inlet for introducing a pretreatment gas into the working station module;

performing a pre-sterilization step, wherein the working station module is moved to a pre-sterilization station; the heat transmission pipe is connected to the heating pipe for heating the working station module; and the suction pipe communicates with the interior of the working station module through the suction port for vacuumizing the working station module;

performing a reagent adding step, wherein the working station module is moved to a reagent adding station; a sterilant is introduced into the working station module through a reagent port; the heat transmission pipe is connected to the heating pipe for heating the working station module; the suction pipe communicates with the interior of the working station module through the suction port for vacuumizing the working station module; and a protective gas pipe communicates with the interior of the working station module through a second gas inlet for introducing a protective gas into the working station module;

performing a sterilization step, wherein the working station module is moved to a sterilization station; the heat transmission pipe is connected to the heating pipe for heating the working station module; and the suction pipe communicates with the interior of the working station module through the suction port for vacuumizing the working station module;

pulse cleaning, wherein the working station module is moved to a cleaning station; the heat transmission pipe is connected to the heating pipe for heating the working station module; the suction pipe communicates with the interior of the working station module through the suction port for vacuumizing the working station module; and the protective gas pipe communicates with the interior of the working station module through the second gas inlet for introducing a second protective gas into the working station module; and performing a discharging step, wherein the working station module is moved to a discharging station; and the material after sterilization is taken out of the material port.

* * * * *